US010070821B2

(12) United States Patent
Leonardi et al.

(10) Patent No.: US 10,070,821 B2
(45) Date of Patent: Sep. 11, 2018

(54) INTRAOCULAR PRESSURE MEASURING AND/OR MONITORING SYSTEM WITH INERTIAL SENSOR

(75) Inventors: Matteo Leonardi, Pully (CH); Jean-Marc Wismer, Lausanne (CH)

(73) Assignee: Sensimed SA, Lausanne (CH)

( * ) Notice: Subject to any disclaimer, the term of this patent is extended or adjusted under 35 U.S.C. 154(b) by 648 days.

(21) Appl. No.: 14/402,342

(22) PCT Filed: May 21, 2012

(86) PCT No.: PCT/EP2012/059413
§ 371 (c)(1),
(2), (4) Date: Nov. 20, 2014

(87) PCT Pub. No.: WO2013/174414
PCT Pub. Date: Nov. 28, 2013

(65) Prior Publication Data
US 2015/0150510 A1   Jun. 4, 2015

(51) Int. Cl.
*A61B 5/00* (2006.01)
*A61B 3/16* (2006.01)
*A61B 3/00* (2006.01)

(52) U.S. Cl.
CPC ............ *A61B 5/721* (2013.01); *A61B 3/0025* (2013.01); *A61B 3/16* (2013.01); *A61B 5/0004* (2013.01); *A61B 5/6821* (2013.01); *A61B 5/6823* (2013.01); *A61B 5/6833* (2013.01)

(58) Field of Classification Search
CPC ........ A61B 3/0025; A61B 3/16; A61B 5/6833
See application file for complete search history.

(56) References Cited

U.S. PATENT DOCUMENTS

| 2003/0078487 | A1 | 4/2003 | Jeffries et al. | |
|---|---|---|---|---|
| 2013/0158381 | A1* | 6/2013 | Rickard | A61B 3/16 600/399 |
| 2013/0235328 | A1 | 9/2013 | Cauvet et al. | |

FOREIGN PATENT DOCUMENTS

| WO | 2003/078487 A1 | 9/2003 | |
|---|---|---|---|
| WO | 2011/035262 A1 | 3/2011 | |
| WO | WO 2011083105 A1 * | 7/2011 | ............... A61B 3/16 |

OTHER PUBLICATIONS

Leonardi, Matteo, et al. "Wireless contact lens sensor for intraocular pressure monitoring: assessment on enucleated pig eyes." Acta ophthalmologica 87.4 (2009): 433-437.*
ISR and Written Opinion for PCT/EP2012/059413, dated Jan. 3, 2013.

* cited by examiner

*Primary Examiner* — Daniel Cerioni
*Assistant Examiner* — Yasmeen S Warsi
(74) *Attorney, Agent, or Firm* — Bachman & LaPointe, P.C.

(57) ABSTRACT

An intraocular pressure measuring and/or monitoring system comprises an intraocular pressure measuring device (1) comprising a support (3) and a pressure sensor (2) united with the support. The support (3) is configured for placing the pressure sensor (2) in contact with an eye (8) of a user for sensing the intraocular pressure (IOP) of the eye. A portable recording device (6) is configured for communicating with the intraocular pressure measuring device (1) and for storing data received from the intraocular pressure measuring device. The system further comprises an inertial and/or environmental sensor (9).

14 Claims, 5 Drawing Sheets

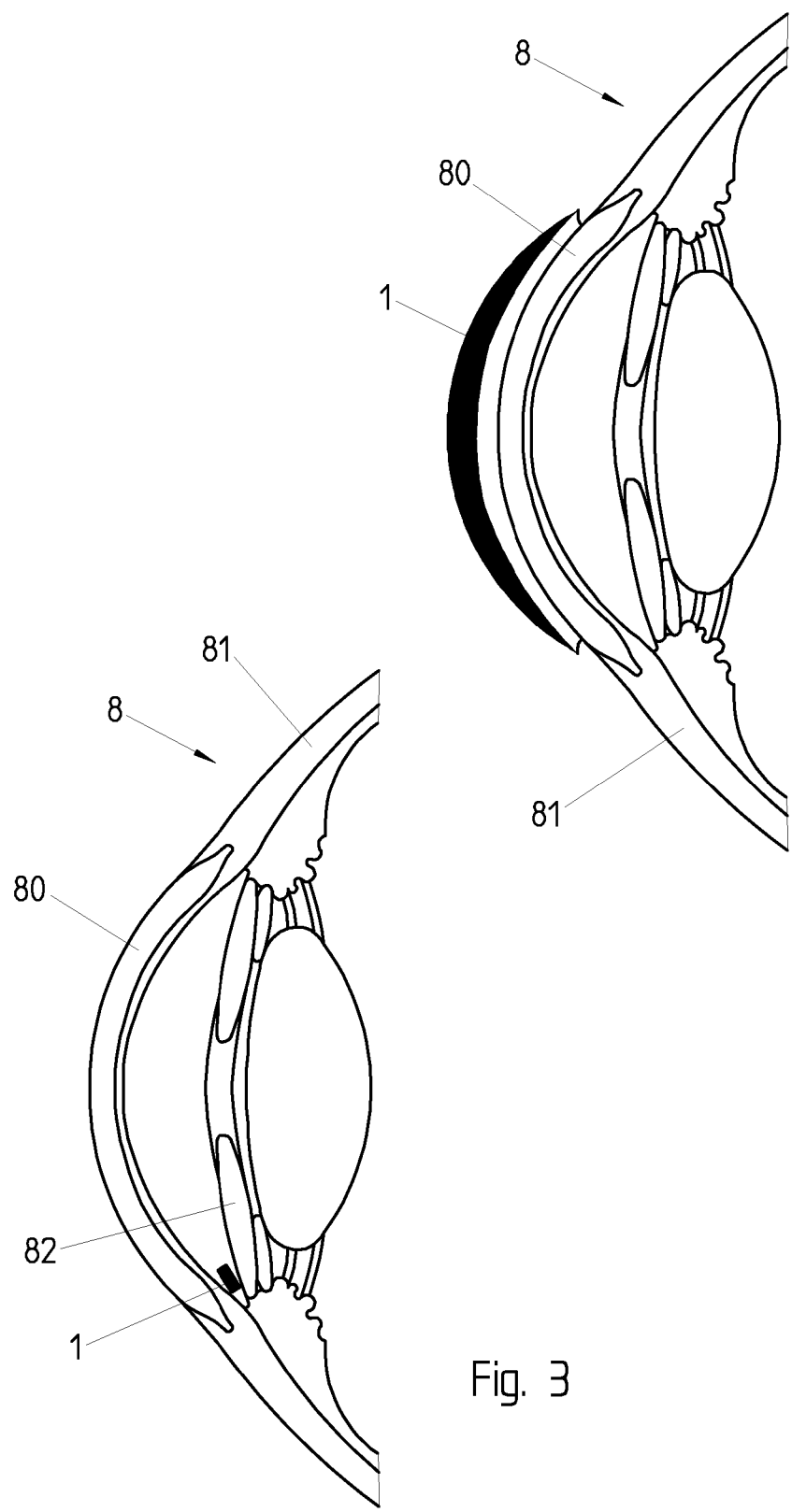

INTRAOCULAR PRESSURE MEASURING AND/OR MONITORING SYSTEM WITH INERTIAL SENSOR

BACKGROUND

The present invention relates to a system for measuring and/or monitoring the intraocular pressure (IOP). The present invention relates in particular to a system comprising a device that can be placed on or in the eye of a user to monitor intraocular pressure over an extended period of time, wherein the system further comprises inertial and optionally environmental sensors in order to allow correlating the thus collected inertial and optionally environmental information with the intraocular pressure measurements.

Glaucoma is a widespread disease characterized by an elevated intraocular pressure (IOP). This elevated IOP produces a gradual loss of peripheral vision. There is therefore a need to have a detailed knowledge of IOP in glaucoma patients in order to provide reliable diagnostics or for setting up new therapies.

There are several types of devices that are commonly used for measuring IOP on patients. Some devices are configured for single measurements and are usually bulky fixed equipments. A pressure sensor is applied on the patient's eye with a determined pressure for a short period of time.

Other equipments allow IOP measurement over extended periods of time, for example some hours, days or more. These devices often comprise a miniaturized pressure sensor, for example in the form of a MEMS, that is worn by the patient during the entire measuring time period. The pressure sensor is for example integrated into or attached to a contact lens worn by the patient, or mounted on a support configured to be directly implanted into the eyeball. The pressure sensor continuously measures the IOP as long as it is in contact with the eye, and the measured pressure values are transmitted to and for example stored by a receiver over a wired or a wireless communication link.

An advantage of such pressure measuring devices or systems is that they allow measuring the IOP of a patient over an extended period of time, thereby allowing monitoring the evolution of the IOP during the day, allowing for example measuring possible pressure differences depending on whether the patient is awake or asleep, tired or not, etc.

WO 2011/035262 and US 2003/0078487 for example describe implantable intraocular pressure monitoring devices, and WO 2011/083105 describes an intraocular pressure monitoring device united to a contact lens, that all communicate wirelessly with a remote device. These devices may for example be used to measure intraocular pressure over extended time periods.

However, it might be sometimes difficult to analyze some of the measured IOP variations that can be due to external factors, for example the patient's physical activity and/or environment at the time of IOP measurement.

SUMMARY

An aim of the present invention is thus to provide an intraocular pressure measuring and/or monitoring system that allows a more accurate analysis of the IOP measurements taken over extended period of times.

Another aim of the present invention is to provide an intraocular pressure measuring and/or monitoring system that allows a more comprehensive analysis of IOP measurements done during an extended IOP monitoring period of time.

These aims and other advantages are achieved by a system and a device comprising the features of the corresponding independent claim.

These aims and other advantages are achieved in particular by an intraocular pressure measuring and/or monitoring system, comprising an intraocular pressure measuring device comprising a support and a pressure sensor united with the support, the support being configured for placing the pressure sensor in contact with an eye of a user for sensing the intraocular pressure (IOP) of the eye, a portable recording device configured for communicating with the intraocular pressure measuring device and for storing data received from the intraocular pressure measuring device, wherein the system further comprises an inertial sensor.

The support is for example a contact lens or a support configured to be implanted in the eye.

In embodiments, the intraocular pressure measuring and/or monitoring system further comprises an environmental sensor.

In embodiments, the inertial sensor is located in the intraocular pressure measuring device.

In other embodiments, the inertial sensor is located in the portable recording device.

The portable recording device for example comprises an antenna for wirelessly communicating with the intraocular pressure measuring device. The antenna is for example located in a patch adapted to surround the eye of a user when the intraocular pressure measuring and/or monitoring system is worn by the user. The inertial sensor is then for example located in the patch, or in a communication module forming an interface to the antenna, the communication module being adapted to be placed on a user's head when the intraocular pressure measuring and/or monitoring system is worn by the user.

In embodiments, the portable recording device is configured for communicating with the inertial sensor and for storing data received from the inertial sensor.

In embodiments, the intraocular pressure measuring and/or monitoring system comprises at least two inertial sensors. The at least two inertial sensors for example comprise a first and a second inertial sensor, the first inertial sensor being located in a housing of the portable recording device adapted to be worn against the chest of a user, and the second inertial sensor being located in a communication module adapted to be placed on a user's head when the intraocular pressure measuring and/or monitoring system is worn by the user.

These aims and other advantages are also achieved in particular by an intraocular pressure measuring device comprising a support and a pressure sensor united with the support, the support being configured for placing the pressure sensor in contact with an eye of a user for sensing the intraocular pressure (IOP) of the eye, wherein the device further comprises an inertial sensor.

The support is for example a contact lens or a support configured to be implanted in the eye.

With the inertial sensor and optionally an environmental sensor, information is collected about movements and/or physical activity and optionally the environment of the patient during the IOP measuring and/or monitoring period. The information obtained from the inertial sensor and optionally the environmental sensor, which is attached to the user, preferably close to the pressure sensor, during the IOP measuring and/or monitoring period, for example includes one or more parameters from the group comprising the physical activity of the patient, the intensity of the physical activity, the position of the patient, etc., and optionally the ambient temperature, the local atmospheric pressure, the altitude, etc. The system and/or device of the invention thus allows correlating information on IOP with information on patient activity and optionally environment measured and/or monitored during the same period of time in order for example to analyse the effect of one or more of the measured inertial and optionally environmental parameters on the IOP.

In embodiments, the intraocular pressure measuring and/or monitoring system of the invention comprises an inertial sensor detecting and/or measuring the position and/or the movements of the user, for example accelerations or shocks to which the user may be submitted, the position of the user, in particular of the user's head in order to determined whether the user is standing, sitting or laying down, etc. The inertial sensor is for example a MEMS comprising accelerometers and/or gyroscopes allowing the measurement of linear accelerations along three orthogonal directions and/or angular rates around three orthogonal rotation axis.

Using two inertial sensors, for example a first one located against or near the chest of a user, and a second one located on or near the head of the user furthermore allows for example determining the relative position of the user's head and body.

In embodiments, the intraocular pressure measuring and/or monitoring system of the invention further comprises an environmental sensor, for example a barometer, an altimeter, a GPS receiver and/or a thermometer, for recording corresponding information about the environment of the patient wearing the intraocular pressure measuring and/or monitoring system.

In embodiments, the intraocular pressure measuring and/or monitoring system of the invention comprises one or more inertial sensors and one or more environmental sensors.

BRIEF DESCRIPTION OF THE DRAWINGS

The present invention will be better understood with the help of the following description illustrated by the figures, where:

FIG. 2 is a schematic cut view of an eye wearing the intraocular pressure measuring device of FIG. 1;

FIG. 3 is a schematic cut view of an eye wearing an intraocular pressure measuring device according to another embodiment of the invention;

DETAILED DESCRIPTION

In embodiments, the intraocular pressure measuring and/or monitoring system of the invention comprises an intraocular pressure measuring device to be placed on or in the eye of a patient for measuring the intraocular pressure of said eye, and a portable recording device for communicating with the intraocular pressure measuring device and storing information collected by the intraocular pressure measuring device during IOP monitoring phases.

Figure 1:
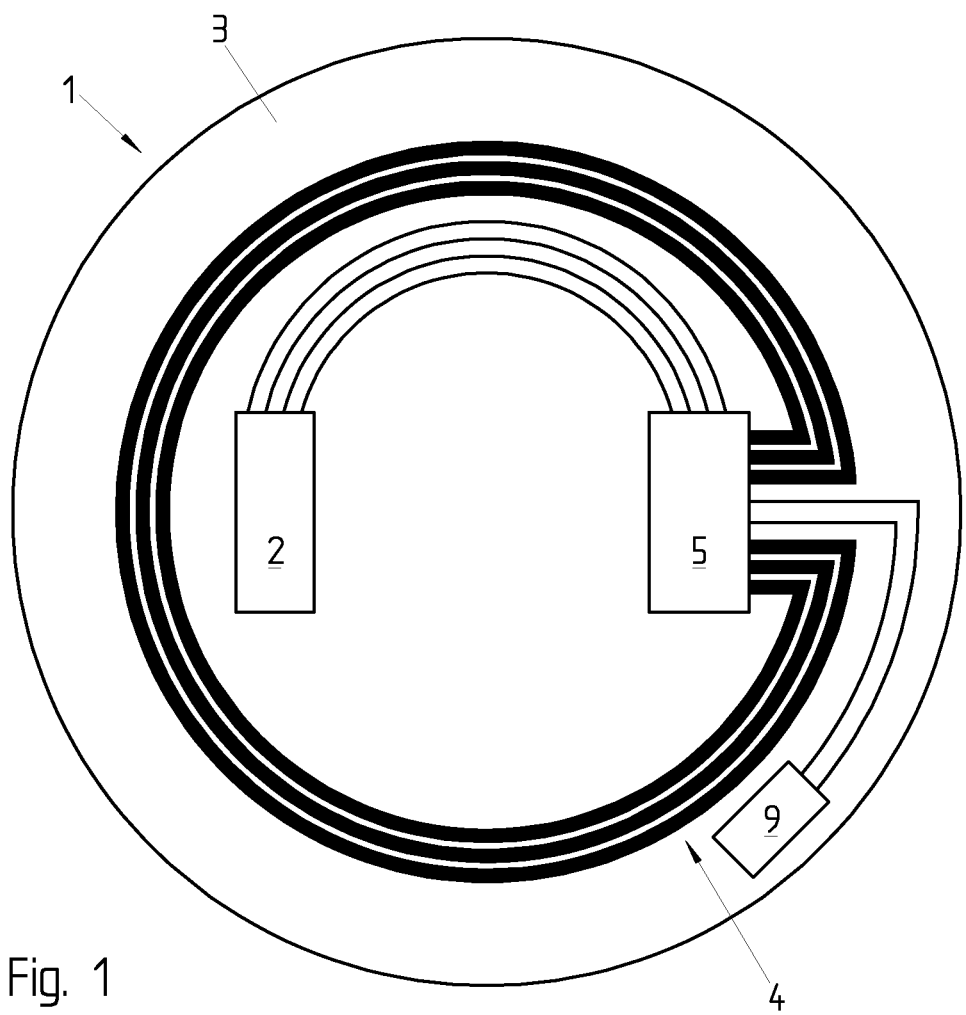
FIG. 1 shows an intraocular pressure measuring device according to an embodiment of the invention.

In an embodiment illustrated in FIG. 1, the intraocular pressure measuring device 1 comprises a pressure sensor 2 united with a support in the form of a contact lens 3, for example a soft contact lens. The pressure sensor 2 is located such that, when the contact lens 3 is worn by a user, the pressure sensor 2 is applied against an eyeball of the user for sensing the intraocular pressure (IOP) of the corresponding eye.

FIG. 2 schematically illustrates an example of an IOP measuring device 1 having a support in the form of a contact lens, placed on an eye 8 of a patient or user. According to the illustrated example, the user wears the IOP measuring device 1 just like a standard contact lens, wherein the contact lens is centered on the cornea 80. Other types of IOP measuring device having a support in the form of a contact lens are however possible within the frame of the invention, for example IOP measuring devices wherein the support is designed to be placed on the sclera, for example under the eyelid, which is not represented in FIG. 2.

Alternatively, and with reference to FIG. 3, the intraocular pressure measuring device 1 is an implantable device, whereas the support is adapted to be implanted in the eye, for example between the cornea 80 and the iris 82, or in any other appropriate location within a patient's eye 8. Implanting the implantable IOP measuring device 1 is an ambulatory surgical operation, which is usually performed by a medical doctor.

According to embodiments of the invention, and with reference to FIG. 1, the intraocular pressure measuring device 1 further comprises an inertial sensor 9 for sensing for example the position, orientation and/or movements of the eye of the user when the user wears said device 1.

As explained below, according to other embodiments of the invention, the inertial sensor is located in other parts of the intraocular pressure measuring and/or monitoring system, for example in the portable device.

The inertial sensor 9 is for example an inertial sensor comprising accelerometers and/or gyroscopes for detecting accelerations along three axis orthogonal to each other (three dimensional accelerator) and/or angular rates around three rotation axis orthogonal to each other (three dimensional gyroscope), thus allowing detecting and/or measuring the movements of a user wearing said inertial sensor 9.

In other embodiments the inertial sensor 9 is for example an inertial sensor comprising a position and/or orientation sensor for determining the position and/or the position of a user or at least a part of a user, for example the head of a user, when said user wears said inertial sensor 9.

In embodiments the intraocular pressure measuring device 1 further comprises an environmental sensor comprising for example a barometer, a thermometer, an altimeter and/or a GPS receiver for measuring the ambient atmospheric pressure, the ambient temperature and/or the temperature of the eye, the altitude and/or the geographic position of the intraocular pressure measuring and/or monitoring system of the invention.

In embodiments, the intraocular pressure measuring and/or monitoring system of the invention comprises a plurality of inertial sensors and optionally environmental sensors, possibly located in different parts of the system, for example of the IOP measuring device and/or of the portable device, the location of each sensor depending for example on its size and/or on its power requirement and/or on its nature.

Due to size constraints, one or more inertial and/or environmental sensors are MEMS, in particular when said inertial and/or environmental sensor is located in the IOP measuring device to be worn on or in the eye.

In embodiments, as illustrated for example in FIG. 1, the intraocular pressure measuring device 1 further comprises, united with the contact lens 3, a microcontroller 5 in electrical contact with the pressure sensor 2 and with the inertial sensor 9 for powering the sensors 2, 9 and/or for receiving electrical signals from the pressure sensor 2 that correspond to the measured pressure and/or for receiving electrical signals from the inertial sensor 9 that correspond to the measured inertial parameters. The IOP measuring device 1 also comprises an antenna 4 in electrical contact with the microcontroller 5 for wirelessly transmitting data, for example data received from the sensors 2, 9, to a remote equipment, for example to the portable device of the system of the invention, which is not represented in FIG. 1.

In an embodiment, the intraocular pressure measuring device 1, in particular the microcontroller 5 and/or one or both sensors 2, 9, is preferably wirelessly inductively powered through the antenna 4, for example by the portable device. In a variant embodiment, the pressure measuring device comprises a power source, for example a battery or micro fuel cell or a wireless energy source like infrared or solar cells, for powering the microcontroller and/or one or both sensors. The power source is for example located on or inside the support, or on an external device, in which case it is for example electrically connected through thin and insulated electrical wires to the microcontroller and/or to the sensors.

The pressure sensor 2 is for example a miniaturized pressure sensor comprising a piezoresistive silicon micromachined pressure sensor on a ceramic or silicon carrier. Other types of pressure sensors are however possible within the frame of the invention, for example strain gage pressure sensors that comprises thin resistance elements that are elongated or retracted under the effect of the IOP, or any other adapted pressure sensor. The choice of the most appropriate pressure sensor will depend for example on the nature and size of the support, on the location of the IOP measuring device when worn by a user, on the desired measurement accuracy, etc.

In variant embodiments, the pressure sensor and the inertial sensor are manufactured as a single device, for example a single MEMS performing both functions.

With reference to FIG. 1, measuring the pressure sensed by the pressure sensor 2 is for example performed in that the microcontroller 5 powers the pressure sensor 2 with a given voltage and receives in return from the pressure sensor 2 an electrical signal that corresponds to the sensed pressure, for example an electrical signal whose magnitude depends from the electrical resistance of the circuit formed by the piezoresistors. The received signal is stored and/or processed for example in the microcontroller 5 for determining the measured pressure. The pressure measurement is for example performed at regular intervals, for example each time the intraocular pressure measuring and/or monitoring device 1 is inductively powered by an external device, for example an external RFID reader or similar. In variant embodiments, the pressure measurement is performed for example continuously or at randomly spaced intervals.

In embodiments, for example in embodiments wherein the inertial sensor 9 is located within the pressure measuring device 1, the inertial sensor 9 is powered simultaneously with the pressure sensor 2 and the measurement of the inertial parameters is performed similarly as described above in relation with the intraocular pressure measurement.

In other embodiments, for example in embodiments wherein the inertial sensor is located in other locations of the IOP measuring and/or monitoring system of the invention, for example in the portable device, the measurement of the inertial parameters is performed continuously or at any other appropriate frequency. The inertial sensor is for example continuously powered from an electrical source, for example batteries or accumulators, located in the portable device.

With reference to FIG. 1, the contact lens 3 is for example a soft contact lens made of a transparent hydrogel containing water in a concentration greater than 10%, or of any other appropriate material having similar mechanical and/or optical properties, for example a flexible polysiloxane, a silicone elastomer, a pure soft silicone containing water in a concentration less than 0.5% or silicone-hydrogel. The contact lens 3 has a typical diameter of 14.1 mm and a typical radius of curvature between 8.4 and 9 mm and is for example softer than the surface of the eyeball of a user, such that when the pressure measuring and/or monitoring device 1 is worn by a user, the contact lens 3 is slightly deformed, for example stretched, to adapt its shape to the shape of the eyeball, in particular to the curvature of the user's eye. This deformation of the contact lens 3 provides for a regular contact and a strong adherence between the contact lens 3 and the user's eyeball across the surface of the contact lens which adapts to the shape of the eye, thus providing for a close and constant contact between the pressure sensor 2 placed within this area and the eyeball.

Optionally, the pressure measuring device 1 further comprises additional and/or other measuring devices such as for example an ElectroRetinoGraph, a chemical analysis sensor and/or a second pressure sensor of the same or of another type as the first one.

Figure 4:
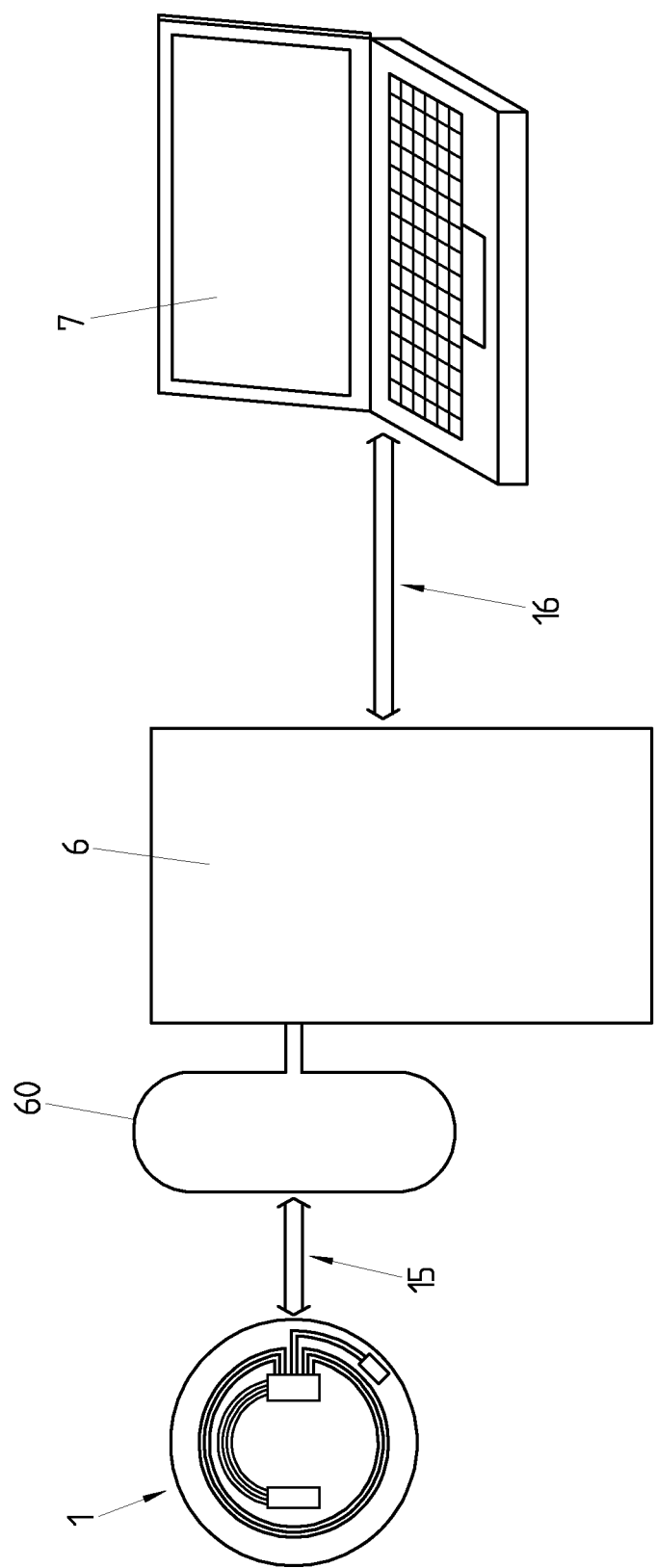
FIG. 4 is a schematic representation of an example of an intraocular pressure measuring and/or monitoring system of the invention.

FIG. 4 is a schematic representation of an intraocular pressure measuring and/or monitoring system according to an embodiment of the invention. According to the illustrated embodiment, the intraocular pressure measuring and/or monitoring system comprises an intraocular pressure measuring device 1, for example an intraocular pressure measuring device 1 with a support in the form of a contact lens, and a portable recording device 6 for communicating with the pressure measuring device 1 and storing the information collected during the IOP monitoring phases.

The portable recording device 6 comprises a first communication interface for communicating with the pressure measuring device 1. The first communication interface is for example a wireless communication interface comprising an antenna 60, for example a loop antenna, which is advantageously placed near the pressure measuring device 1 when the pressure measuring device 1 is worn by a user.

The portable recording device 6 comprises a second communication interface 16 for communicating with a remote computing device 7, for example a personal computer, for storing, analyzing, computing and/or displaying the data collected and stored by the portable communication device 6.

Figure 5:
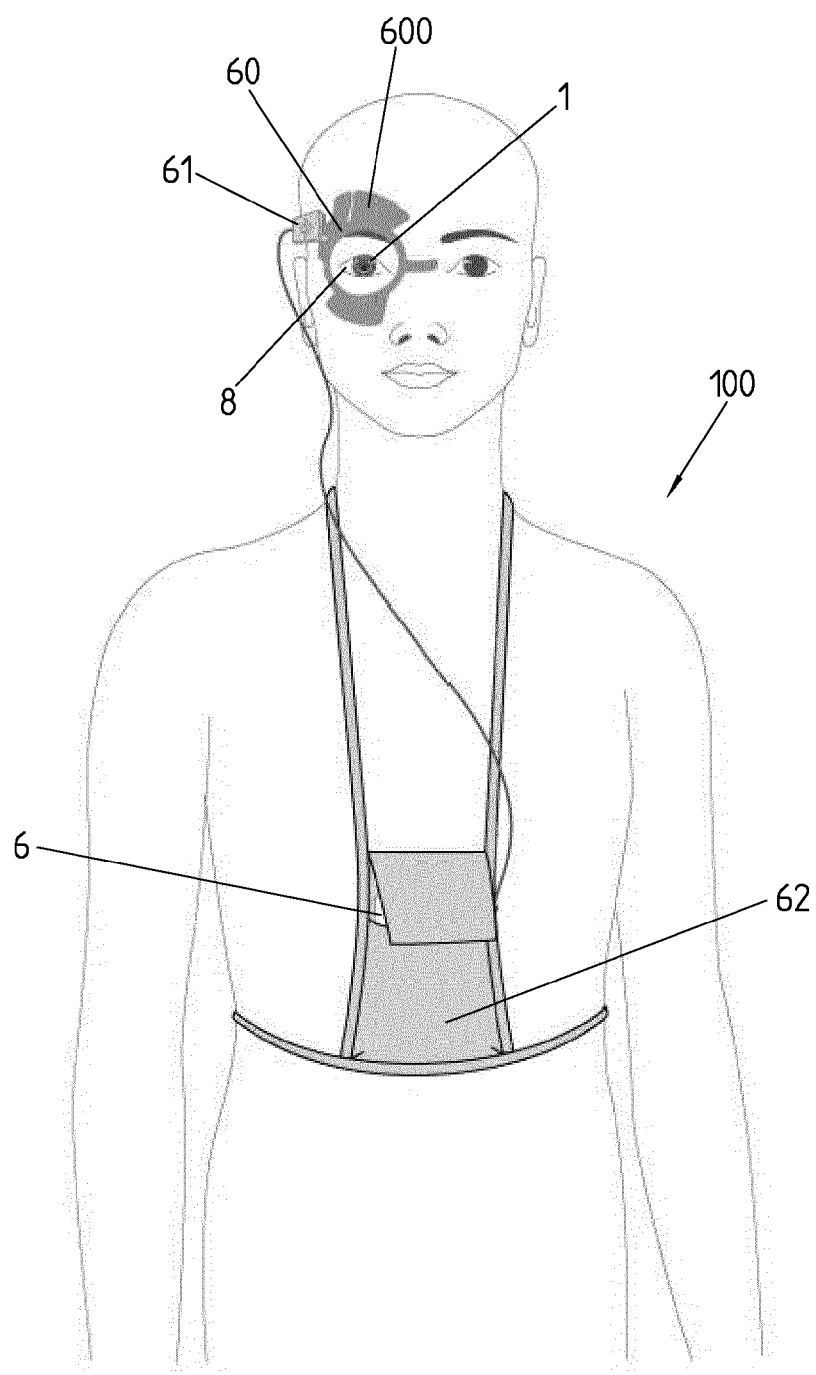
FIG. 5 shows a user wearing an intraocular pressure measuring and/or monitoring system according to an embodiment of the invention.

When monitoring IOP, the user wears the pressure measuring and/or monitoring system of the invention as showed by way of an illustrative but in no way limiting example in FIG. 5. Accordingly, the user 100 wears the intraocular pressure measuring device 1 on or in an eye 8 and carries the portable recording device 6, for example in a pocket 62 hanging from his or her neck and for example secured with straps on his or her chest. Any other adapted solution is however possible within the frame of the invention for the user 100 to carry the portable device 6, preferably without significantly impacting his comfort.

The antenna 60 is preferably placed as close as possible to the user's eye 8 wearing the pressure measuring device 1 in order to allow the establishment of the first wireless communication channel between the pressure measuring device 1 and the recording device 6. Preferably, the antenna 60 is furthermore oriented in a plane as parallel as possible to the plane of the antenna of the pressure measuring device 1 in order to allow for an efficient powering of the microprocessor, of the pressure sensor and/or of the inertial sensor over the first communication channel, which is for example a close distance inductive communication channel. The antenna 60 is for example integrated into a patch 600 surrounding the eye 8, for example into a disposable, flexible and hypoallergenic patch, which is worn by the user during the IOP monitoring periods.

Alternatively, the antenna of the portable device is for example integrated into eyeglasses and/or in a cap or another piece of clothing or accessory worn by the user during IOP monitoring periods. Other means are however possible within the frame of the invention for placing the antenna of the portable device at a suitable distance from the pressure measuring device when the latter is worn by a user.

Preferably, the antenna 60 of the portable device 6 is centered with the antenna of the pressure measuring device 1 when the pressure measuring device 1 and the portable recording device 6 are both worn by the user 100. The diameter of the antenna 60 of the portable recording device 6 is preferably larger than the diameter of the pressure measuring device 1. The shape of the antenna 60 of the portable recording device 6 is for example round, oval, rectangular, or any other appropriate shape. The shape of the antenna 60 of the portable recording device 6 is preferably adapted to the shape of the element, for example the patch 600, the eyeglasses, the piece of garment, etc., to which it is attached.

In embodiments, the inertial sensor, which is not represented in FIG. 5, is comprised in the intraocular pressure measuring device 1, for example attached to the contact lens or to the implantable support of the IOP measuring device 1. An advantage of locating the inertial sensor in the intraocular pressure measuring device 1 is that the inertial sensor is located directly on or inside the eye 8 and close to the pressure sensor of the pressure measuring device 1 that senses the IOP. The inertial sensor is thus subjected to the same inertial conditions as the eye 8 of the patient 100 and/or as the pressure sensor of the IOP measuring device 1. Accordingly, the inertial parameters measured by the inertial sensor correspond directly to the ones that may have an influence on the measured IOP.

In other embodiments, the inertial sensor is comprised in the portable device 6. Locating the inertial sensor in the portable device 6 allows the use of a sensor larger than a sensor to be embedded in the intraocular pressure device 1. When located in the portable device 6, the inertial sensor is preferably powered over a wired link from the source of electric energy of the portable device 6.

The inertial sensor is for example located near the antenna 60 of the portable device 6, for example in the patch 600, in spectacles carrying the antenna, or a in a communication module 61 forming an interface to the antenna 60 and located on the user's head when the user wears the system of the invention. An advantage of locating the inertial sensor on the head of the user 100 when the user wears the system of the invention is that the inertial sensor is subjected to inertial conditions that are identical or very similar to the ones to which the IOP pressure sensor and the monitored eye are subjected.

Alternatively, the inertial sensor is located in a housing of portable device 6 that is worn for example in a pocket 62 located for example on the chest of the user 100 when the user wears the system of the invention, or in any other appropriate part of the portable device 6, depending for example on the nature of the measurement or measurements to be performed by the inertial sensor. This location of the inertial sensor allows the use of even larger and/or more sophisticated sensors with possibly higher power consumption.

Figure 6:
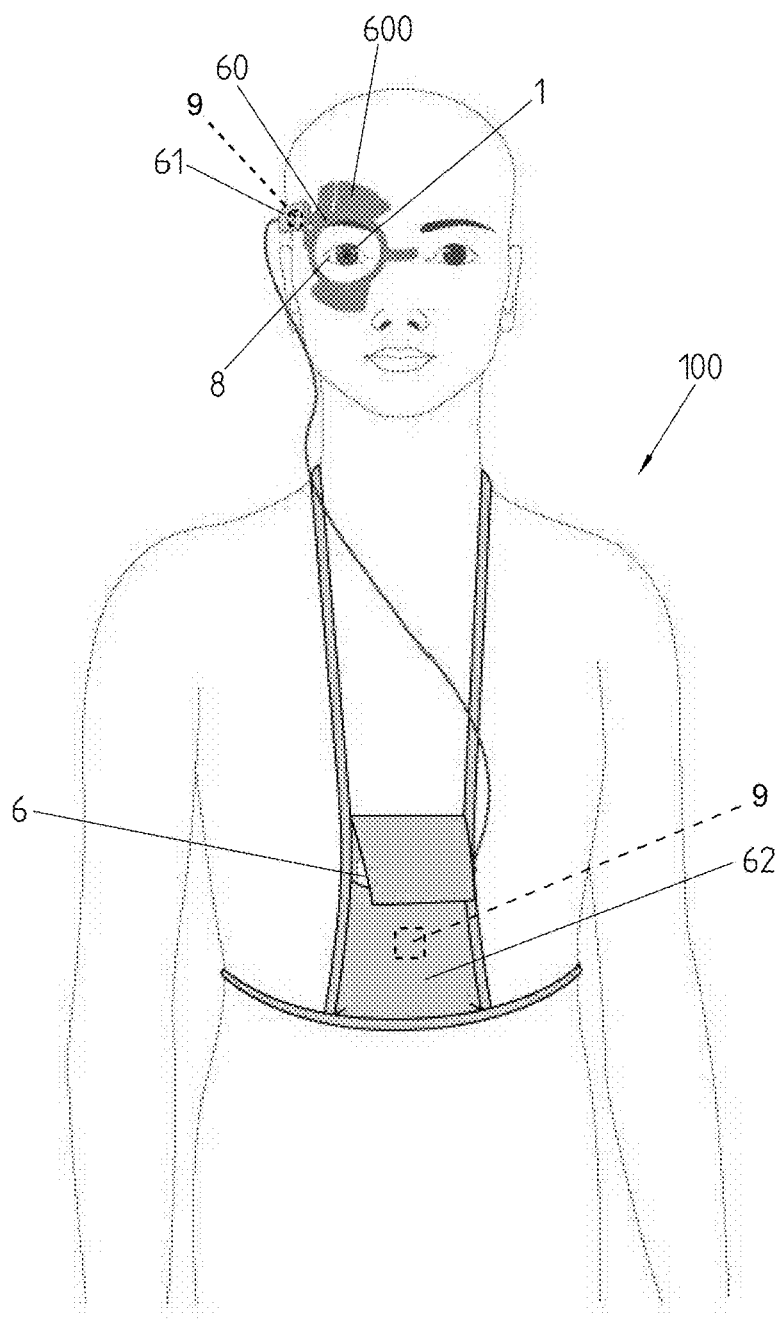
FIG. 6 shows a user wearing a second intraocular pressure measuring and/or monitoring system according to an embodiment of the invention.

In still other embodiments, the intraocular pressure measuring and/or monitoring system of the invention comprises at least two inertial sensors that are located in different parts of the system and/or of the portable device 6 (FIG. 6).

According to embodiments, while monitoring IOP, the portable recording device 6 powers the pressure measuring device 1 through the first communication channel at for example regularly spaced time intervals and collects data sent by the microprocessor through the antenna of the pressure measuring device 1. Collected data for example comprises electrical signals from the pressure sensor and/or an IOP value calculated by a microprocessor of the pressure measuring device 1. In embodiments, collected data also comprises electrical signals from the inertial sensor and/or values of one or more inertial parameters, calculated by a microprocessor of the pressure measuring device 1. The collected data is stored in internal memory of the portable recording device 6. The intraocular pressure and/or one or more inertial parameters, are for example measured at a frequency of 10 to 20 Hz during 10 to 60 seconds every 5 to 10 minutes. This allows a precise monitoring of the IOP variations over extended periods of time, including at night, while the user is asleep.

Preferably, the measurement frequency of the one or more inertial parameters is the same as the measurement frequency of the IOP, and the measurements are even more preferably simultaneous or almost simultaneous. However, according to embodiments of the invention, the measurement scheme of the one or more inertial parameters is different from the measurement scheme of the intraocular pressure. This is for example the case when the inertial sensor is located in the portable device 6 and is continuously powered, whereas the measurement is for example performed continuously. Other measurement schemes are however possible within the frame of the invention.

At some preferably predefined moments in time, for example once a day, once a week or once a month, the user and/or a practitioner connects the portable recording device 6 to the remote computing device, for example a personal computer, over a second, preferably wireless, communication channel, for example a Bluetooth communication channel. The second communication channel can however also be a wired communication channel, for example a USB or any other appropriate communication channel. The data collected and stored in the internal memory of the portable recording device 6 is then transferred over the second communication channel to the computing device for further analysis and/or computing by the user and/or by the practitioner.

The IOP measurements are correlated, for example by the computing device 7, with the inertial measurements, for example by displaying all measurements in a single graph having the same time baseline, or any other appropriate representation. IOP variation analysis can then be performed and, for example at least partly automatically, correlated with the simultaneous variations of the measured inertial parameters, in order for example for a practitioner to analyze the effects of these parameters on the IOP.

In variant embodiments, the intraocular pressure measuring and/or monitoring system of the invention comprises two pressure measuring devices in order to allow simultaneously monitoring both eyes of a patient, for example over extended periods of time. Preferably, both pressure measuring devices simultaneously and/or alternately communicate with the same portable recording device 6 that for example is connected to and/or comprises two antennas. Accordingly, the portable recording device preferably stores or records data received from both intraocular pressure measuring devices.

The invention claimed is:

1. An intraocular pressure measuring system, comprising: an intraocular pressure measuring device comprising a support and a pressure sensor united with said support, said support being configured for placing said pressure sensor in contact with an eye of a user for sensing the intraocular pressure (IOP) of said eye; and a portable recording device configured for communicating with said intraocular pressure measuring device and for storing data received from said intraocular pressure measuring device, wherein said system further comprises at least two inertial sensors, said at least two inertial sensors comprising a first and a second inertial sensor, said first inertial sensor being located in a housing of said portable recording device configured to be worn against the chest of a user, and said second inertial sensor being located in a communication module configured to be placed on a user's head when said intraocular pressure measuring system is worn by said user.

2. The intraocular pressure measuring system of claim 1, wherein said support is a contact lens.

3. The intraocular pressure measuring system of claim 1, wherein said support is configured to be implanted in said eye.

4. The intraocular pressure measuring system of claim 1, wherein said portable recording device comprises an antenna for wirelessly communicating with said intraocular pressure measuring device.

5. The intraocular pressure measuring system of claim 4, wherein said antenna is located in a patch adapted to surround the eye of a user when said intraocular pressure measuring system is worn by said user.

6. The intraocular pressure measuring system of claim 1, wherein said portable recording device is configured for communicating with said inertial sensor and for storing data received from said inertial sensor.

7. An intraocular pressure measuring device comprising a support and a pressure sensor united with said support, said support being configured for placing said pressure sensor in contact with an eye of a user for sensing the intraocular pressure (IOP) of said eye, wherein said device further comprises at least two inertial sensors, said at least two inertial sensors comprising a first and a second inertial sensor, said first inertial sensor being located in a housing of a portable recording device configured to be worn against the chest of a user, and said second inertial sensor being located in a communication module configured to be placed on a user's head when said intraocular pressure measuring system is worn by said user.

8. The intraocular pressure measuring device of claim 7, wherein said support is a contact lens.

9. The intraocular pressure measuring device according to claim 7, wherein said support is configured to be implanted in said eye.

10. The intraocular pressure measuring device of claim 7, further comprising an environmental sensor.

11. The intraocular pressure measuring system of claim 1, further comprising an environmental sensor.

12. The intraocular pressure measuring system of claim 11, wherein the environmental sensor selected from the group consisting of: a barometer for measuring ambient atmospheric pressure; a thermometer for measuring ambient temperature; an altimeter for measuring altitude; and a global positioning system (GPS) receiver for measuring geographic position.

13. The intraocular pressure measuring system of claim 1, wherein each of the first inertial sensor and the second inertial sensor is selected from the group consisting of gyroscopes and accelerometers.

14. The intraocular pressure measuring system of claim 1, wherein each of the first inertial sensor and the second inertial sensor is a three-axis accelerometer.

* * * * *